(12) United States Patent
Brouwers et al.

(10) Patent No.: US 7,506,542 B2
(45) Date of Patent: Mar. 24, 2009

(54) TACK MEASURING DEVICE

(75) Inventors: Leonardus Antonius Maria Brouwers, Beesel (NL); Robertus Johanes Adam Gorter, Utrecht (NL); Nico Antonius Johannes Hubertus Boonen, Geldrop (NL)

(73) Assignee: Nederlandse Organisatie Voor Toegepast-Natuurwetenschappelijk Onderzoek TNO, Delft (NL)

( * ) Notice: Subject to any disclaimer, the term of this patent is extended or adjusted under 35 U.S.C. 154(b) by 138 days.

(21) Appl. No.: 10/551,076

(22) PCT Filed: Mar. 30, 2004

(86) PCT No.: PCT/NL2004/000215

§ 371 (c)(1),
(2), (4) Date: Jul. 10, 2006

(87) PCT Pub. No.: WO2004/088284

PCT Pub. Date: Oct. 14, 2004

(65) Prior Publication Data

US 2007/0028680 A1 Feb. 8, 2007

(30) Foreign Application Priority Data

Mar. 31, 2003 (NL) .................................. 1023056

(51) Int. Cl.
*G01N 19/04* (2006.01)
(52) U.S. Cl. .................................................. 73/150 A
(58) Field of Classification Search ............... 73/150 A, 73/54.22

See application file for complete search history.

(56) References Cited

U.S. PATENT DOCUMENTS 2,101,322 A 12/1937 Reed .......................... 73/54.22

(Continued)

FOREIGN PATENT DOCUMENTS

EP 1 024 361 A1 8/2000

(Continued)

*Primary Examiner*—Hezron Williams
*Assistant Examiner*—Tamiko D Bellamy
(74) *Attorney, Agent, or Firm*—Leydig, Voit & Mayer, Ltd.

(57) ABSTRACT

A device for measuring the tack of materials, comprising a first cylinder (1) included in a fixed frame (2) and a second cylinder (3) included in a movable yoke (4), whose outer surfaces contact each other via a layer of the material to be tested for tack (8). The yoke (4) is connected with the frame (2) via a connecting element (5) movable about a center. A force sensor (6) is included between the yoke and the movable connecting element or between the frame and the movable connecting element. The output of the force sensor (6) is connected with processing means (7) for processing the measuring signal delivered by the force sensor into a material-specific tack value. In a first calibration step, the first cylinder is coupled with a static mass (11) via coupling means (10). A first correction value, based on the measuring signal delivered by the force sensor, is stored in the processing means. During a second calibration step, the first and second cylinder are contacted with each other without material to be measured. A second correction value, based on the measuring signal delivered by the force sensor, is stored in the processing means. In an actual measuring step, the first and the second cylinder are coupled via a layer of the material to be tested. The measuring signal delivered by the force sensor is processed as a measuring value, taking into account the stored first and/or second correction value.

12 Claims, 2 Drawing Sheets

U.S. PATENT DOCUMENTS

| | | | |
|---|---|---|---|
| 2,762,219 A | 9/1956 | Prentiss | 73/150 R |
| 3,368,399 A | 2/1968 | Wirz | 73/150 R |
| 3,531,986 A | 10/1970 | Van Gastel | 73/150 R |
| 3,559,475 A * | 2/1971 | Dillon et al. | 73/150 R |
| 4,294,111 A | 10/1981 | Rutledge et al. | 73/150 R |
| 5,388,442 A | 2/1995 | Kumar et al. | 73/10 |
| 2002/0194895 A1 | 12/2002 | Germinario et al. | 73/9 |

FOREIGN PATENT DOCUMENTS

| | | |
|---|---|---|
| GB | 1 150 527 | 4/1969 |
| GB | 1 523 380 | 8/1978 |

* cited by examiner

TACK MEASURING DEVICE

FIELD OF THE INVENTION

The invention relates to a device for measuring the tack of materials, comprising a first cylinder which is included in a frame and which is connected with driving means for being able to drive this first cylinder in a first direction, which device further comprises a second cylinder which is included in a movably arranged yoke, which yoke is connected with the frame via force measuring devices which convert the force which the yoke and the frame exert upon each other into a corresponding measuring signal.

BACKGROUND OF THE INVENTION

From a prior patent application in the name of applicant, such a device for measuring the tack of materials is known. The second cylinder is arranged movably with respect to the first cylinder by means of two spring systems, on both sides of the second cylinder. One or both spring systems are provided with a force sensor, which delivers a measuring signal in proportion to the force exerted upon the respective spring system.

For measuring the tack of, for instance, a printing ink, it is uniformly applied to the outer surface of the first cylinder ("main cylinder"). Then, the driving means are activated so that the first cylinder is brought into rotation. Via the outer surface of the first cylinder—and the ink applied thereon, the tack of which is to be determined—the second cylinder ("measuring cylinder") is also brought into rotation. The greater the tack of the ink is, the greater the force exerted upon the spring systems and the greater, therefore, the value of the measuring signal delivered by the force sensor(s).

Although, in practice, the known tack measuring device serves its purpose very well, the accurate setting and adjustment of the device is a time-consuming job. This results from inter alia the bearing and/or alignment of the second cylinder with respect to the first cylinder, in the known device designed by means of leaf spring systems on both sides of the yoke in which the cylinder is included. Further, the positioning of the force sensor(s) on the side of the second cylinder is also unfavorable and this positioning causes systematic inaccuracies.

SUMMARY OF THE INVENTION

It is an object of the present invention to provide improvements which result in an increased system accuracy under operational conditions. It is another object of the present invention to achieve that, in practice, the device can be calibrated, adjusted and operated more easily and more adequately. This results in a greater measuring range, and measuring results which are better reproducible and more reliable.

The improvements in the device for measuring the tack can be achieved in that the yoke (4) is connected with the frame via a connecting element (5) pivotable about at least two mutually non-parallel shafts about a center and that the force measuring means are formed by a force sensor (6) which is connected with this movable connecting element.

Instead of a double bearing with spring assemblies, like in the known device, it has been found that a connection maneuverable, for instance, about multiple shafts (for instance a "Gelenk bearing" or "rod head bearing") can successfully be used, so that, although the thus bearing-mounted yoke has a very great degree of freedom, the second cylinder can excellently be directed, without transverse deviations, to the driving first cylinder ("self-alignment"). Preferably, use is made of a type of ball joint, by means of which one point of yoke is fixed, while the yoke is otherwise freely pivotable about that point. As a result of the absence of undesired transverse forces etc, setting the device is considerably less labor-intensive, more reliable and better reproducible.

The force sensor can be included in the proposed direction between the yoke and the connecting element maneuverable to multiple sides (hereinafter also referred to as "bearing") or between the movable connecting element and the frame.

In order to be able to measure the measuring signal delivered by the force sensor and/or process it into a material-specific tack value, the device preferably comprises processing means with which the force sensor is connected.

In order to be able to calculate the tack value as accurately as possible, preferably, one or more calibration steps are carried out, either as a once-only, initial operation, or regularly, for instance prior to carrying out each new tack measurement.

In a first calibration step, the second cylinder can be coupled via coupling means with a static mass which exerts a static force upon this second cylinder in the direction of the first direction, in which calibration step, a value, based on the measuring signal delivered by the force sensor, is stored in the processing means as a first correction value. Preferably, during the first calibration step, the outer surface of the second cylinder is uncoupled from the outer surface of the first cylinder by means of the "Gelenk" bearing and an uncoupling element, so that only the play and/or friction of the second cylinder is measured.

During a second calibration step, the outer surfaces of the first cylinder and the second cylinder can directly—without intervention of any other material—be coupled with each other while the driving means are activated, during which second calibration step, a value which is based on the measuring signal delivered by the force sensor is stored in the processing means as a second correction value. The second calibration step is preferably carried out at different rotational speeds ("measuring range"). In this manner, the influence of the play and/or friction of the cooperating first and second cylinders is converted into one or more second calibration values (for different cylinder speeds over the whole measuring range), which is taken into account in the calculation of the tack value when an actual tack measurement is carried out by the processing means.

As an alternative for this second calibration step, if desired, it can be chosen not to couple the first and second cylinder with each other directly but via a material of which the tack value is accurately known in advance and which can serve as a calibration value.

During the carrying out by the device of an operational measuring step, the outer surfaces of the first cylinder and the second cylinder are coupled with each other via a layer of the material to be tested for tack which has, for instance, been applied to one of the cylinders. Further, the driving means are activated and the measuring signal delivered by the force sensor is processed by the processing means as a measuring value, taking into account the first and/or second correction value(s) stored in the processing means in the first and second calibration steps respectively.

Hereinafter, the invention will be explained in more detail on the basis of an exemplary embodiment.

DETAILED DESCRIPTION OF THE DRAWINGS

Figure 1:
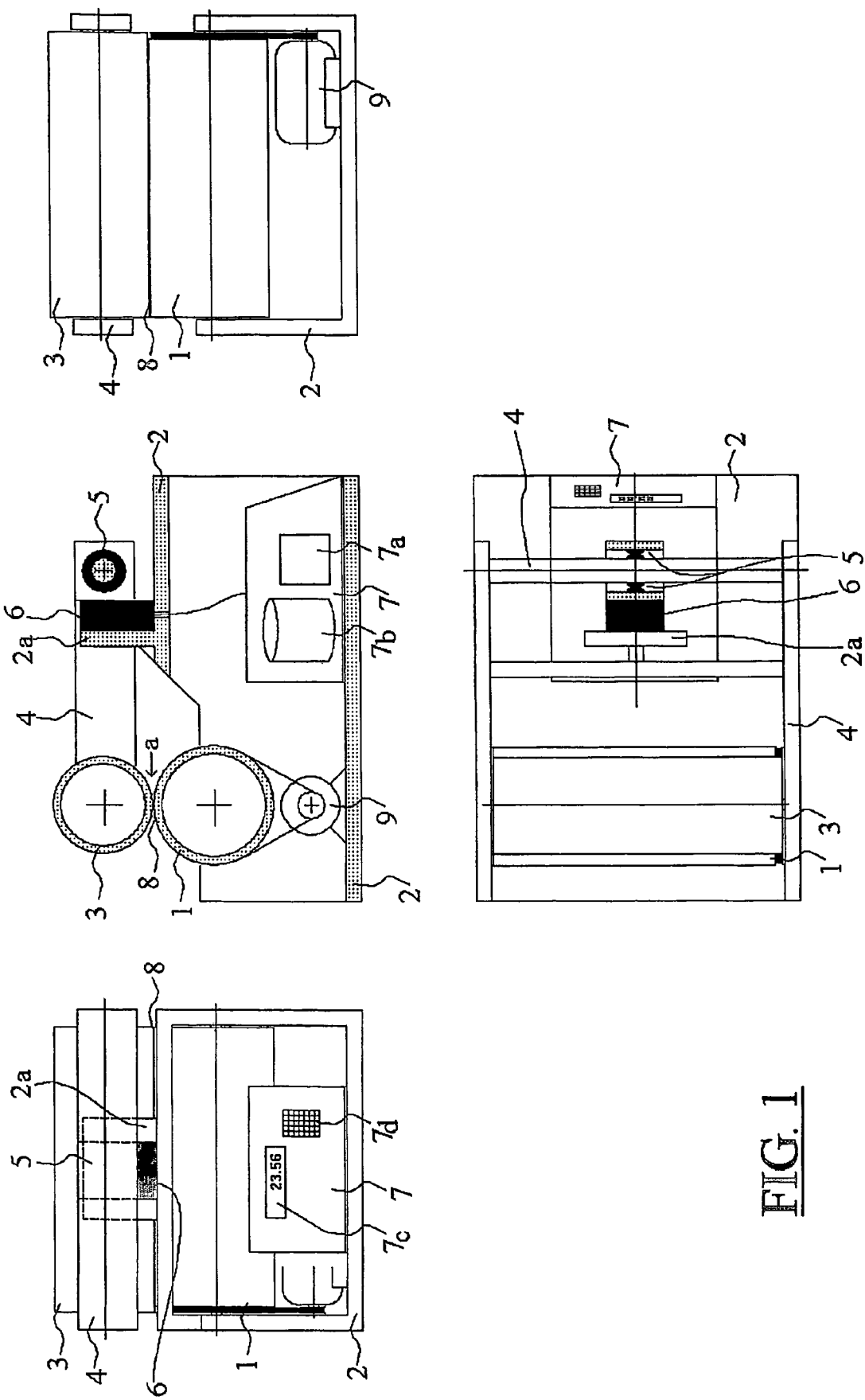
FIG. 1 shows an exemplary embodiment of a device according to the invention in different views and cross sections in European projection respectively.

FIG. 1 shows an implementation example of a device for measuring the tack of, for instance, ink. The device comprises a first cylinder 1 which is included in a fixed frame 2 and which is connected with driving means—an electromotor 9—for being able to drive this first cylinder in a direction (of rotation) a. The device further comprises a second cylinder 3 which ,s included in a movable yoke 4, via which the outer surface of the second cylinder 3 is couplable with that of the first cylinder 1. The yoke 4 is connected with the frame 2 via bearing 5 movable about a center, for instance a ball joint being the sole means to connect yoke 4 and frame 2. The force measuring means are formed by a force sensor 6 which is connected between the movable connecting element 5 and a mounting plate 2a which is part of the frame 2. The force sensor 6, a, for instance, piezoelectric force sensor (load cell), is suitable to convert the force which the yoke 4 and the frame 2 exert upon each other into a corresponding measuring signal which is transmitted to a processing unit 7.

Although it is in principle possible to include the force sensor 6 between the movable yoke 4 and the bearing 5, in the present exemplary embodiment, it was chosen, for constructive reasons, to include the force sensor between the fixed frame 2 and the bearing 5.

The force sensor 6 is connected with the processing unit 7 for processing the measuring signal delivered by the force sensor into one or more material-specific tack values. The measuring unit 7 comprises a processor 7a, a memory 7b, a display 7c and a keyboard 7d.

In order to be able to calculate the tack value as accurately as possible, two calibration steps are carried out, either once-only as part of the production process of the device, or regularly, as periodic maintenance or even prior to carrying out each new tack measurement.

Figure 2:
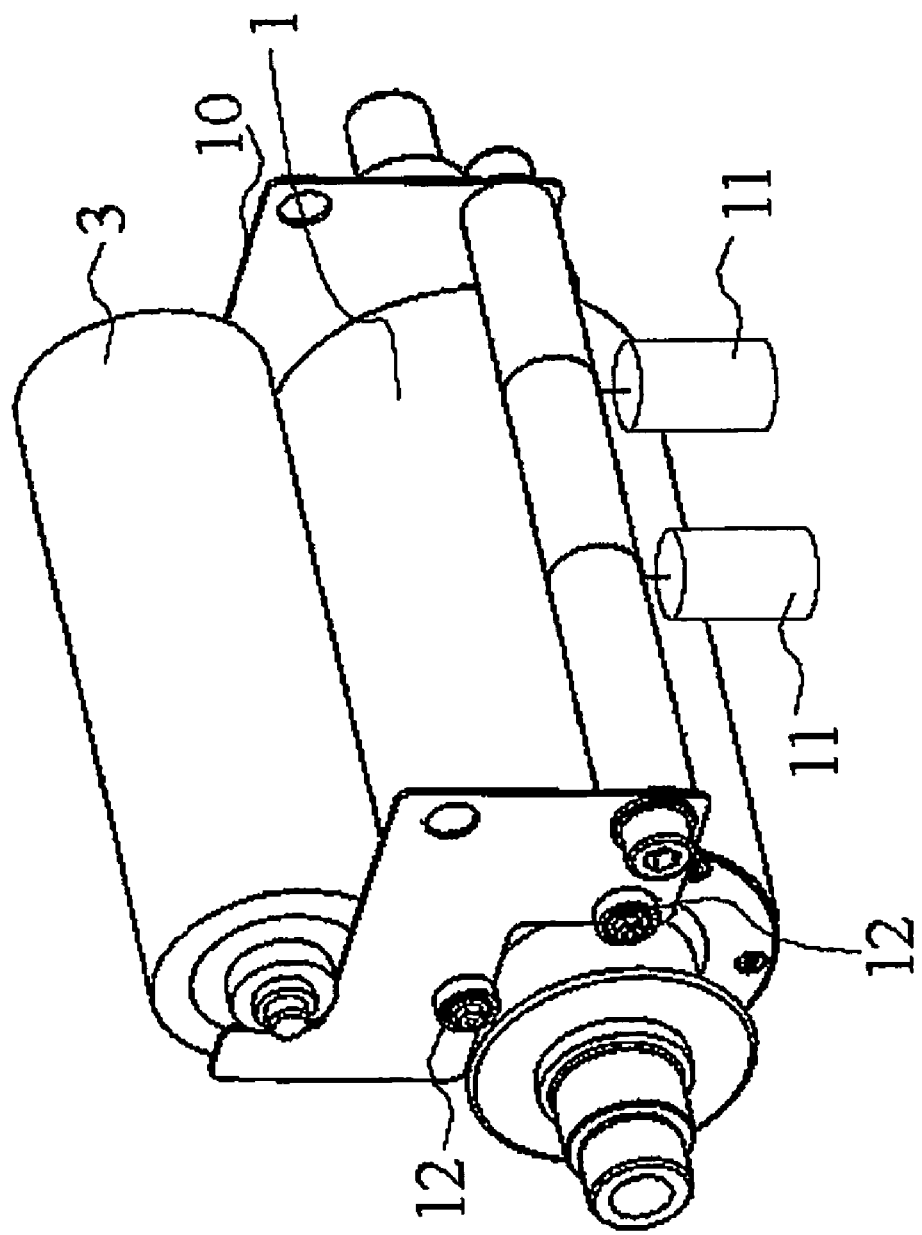
FIG. 2 shows a detail of the device provided with means for carrying out a static calibration.

FIG. 2 shows in which manner a first calibration step can be carried out for the exemplary embodiment of the device diagrammatically shown in FIG. 1. For carrying out the first calibration step—a static calibration of the system—the second cylinder 3 is uncoupled from the first cylinder 1 by pulling the second cylinder upwards by means of a lifting device (not shown). Then, a coupling element 10 is positioned between the shafts of the first and the second cylinder. The coupling element 10 is dimensioned such that the outer surface of the second cylinder 3 stays clear of the outer surface of the first cylinder 1.

From the coupling element 10, standard weights 11 can be suspended. The coupling element 10 is supported, by means of ball bearings 12, upon the first cylinder 1 and, accordingly, upon the fixed frame 2. The weight of the standard weights 11 causes a force upon the second (upper) cylinder 3, which is transmitted via the yoke 4 and the bearing 5 to the force sensor 6 connected with the fixed frame 2 via the mounting plate 2a, which force sensor subsequently delivers a signal value corresponding to this force to the processing unit 7. From, on the one hand, the known weight of the standard weights 11—to be entered via the keyboard 7d if desired—and the proportion of the respective turning moments of the coupling element 10 and, on the other hand, the measuring value which is delivered by the force sensor—to be read out via the display 7c if desired—the static bearing friction of the second cylinder 3 can be calculated by the processor 7a. Either the measuring value delivered by the force sensor 6 under the influence of the standard weights 11 or the friction calculated therefrom by the processor 7a is stored in the memory 7b as a first correction value, from which this value can be read out and then processed during an actual tack measurement.

During a next, second calibration step, the coupling element 10 is removed again and the outer surfaces of the first cylinder 1 and the second cylinder 3 are directly coupled with each other while the driving motor 9 is activated so that the cylinders start to rotate in the indicated arrow direction. In this calibration step, no material to be measured (for instance ink) has been applied yet to the first or second cylinder. In this second calibration step, the measuring signal delivered by the force sensor 6 is received by the processor 7a and either this received measuring signal or a dynamic friction value calculated from the value of this measuring signal is stored in the memory 7b as a second correction value. The stored second correction value can be processed during an actual tack measurement. As has already been noted, a second correction value can be measured at different measuring speeds, that is, at different speeds at which the first cylinder is driven. The different second correction values can be stored in the memory 7b, together with the respective speeds of rotation. In the actual tack measurement to be discussed hereinbelow—which can successively be carried out at different cylinder speeds within a measuring range—then, from the memory 7b, each time, the second correction value can be read out that corresponds to the actual speed of rotation of the first cylinder.

For carrying out an actual tack measurement, to the outer surface of the first cylinder 1 and/or the second cylinder 3, a layer 8 of the material to be tested for tack is applied. Although liquid materials such as ink, paint, glue etc. come to mind first, the use of the device for measurement of the cohesive force of a solid material or measurement of the adhesive force between two solid materials—one applied to one cylinder and the other to the other cylinder—is by no means precluded.

During the actual tack measurement, the outer surfaces of the first cylinder 1 and the second cylinder 2 are contacted with each other, with one of the cylinders or both being covered with a layer 8 of the material or materials to be tested for tack. A driving motor is activated and the cylinders start to rotate. In proportion to the tack of the materials to be tested, a force is exerted upon the movable yoke 4 in the direction of the movement arrows a. Via the yoke 4 and the self-aligning bearing 5, this force is transmitted to the force sensor 6. The measuring signal delivered by the force sensor 6 in proportion to this force is processed by the processing unit 7a as a measuring value, with, for the calculation of the required tack, the first and/or second correction value (which may or may not be related to the actual cylinder speed) stored in the memory during the first and second calibration step respectively being taken into account in the calculation.

The invention claimed is:

1. A device for measuring the tack of materials, comprising:
    a first cylinder which is included in a frame and which is connected with a driver for driving the first cylinder in a first direction;

a second cylinder which is included in a movably arranged yoke, wherein the yoke is connected to the frame via a force measuring sensor which converts the force that the yoke and the frame exert upon each other into a corresponding measuring signal;

characterized in that the yoke is connected with the frame via a connecting element pivotable about at least two mutually non-parallel axes about a center and that the force measuring sensor is formed by a force sensor which is connected with the connecting element.

2. A device according to claim 1, wherein the yoke and the frame are, apart from via surfaces of the first and second cylinder, pivotally coupled with each other solely about a single connection in the connecting element.

3. A device according to claim 1, wherein the force sensor is included between the yoke and the connecting element.

4. A device according to claim 1, wherein the force sensor is included between the frame and the connecting element.

5. A device, according to claim 1, wherein the force sensor is connected with a processor for converting the measuring signal delivered by the force sensor into one or more material-specific tack values.

6. A device according to claim 5, wherein, in a first calibration step, the second cylinder is coupled via coupling component with a static mass which exerts a static force upon this second cylinder in the direction of the said first direction, in which first calibration step, a first correction value, based on the measuring signal delivered by the force sensor, is stored in the processor.

7. A device according to claim 6, wherein, during the first calibration step, the outer surface of the second cylinder is uncoupled from the outer surface of the first cylinder by means of the connecting element and an uncoupling element.

8. A device according to claim 6, wherein, during a second calibration step, the outer surfaces of the first cylinder and the second cylinder are directly coupled with each other while the driver is activated, in which second calibration step, a second correction value, based on the measuring signal delivered by the force sensor, is stored in the processor.

9. A device according to claim 8, wherein the second calibration step is carried out at different speeds of rotation of the first cylinder and the second cylinder, and for each of the different speeds of rotation of the first and second cylinders, the respective second correction value is stored in the processor.

10. A device according to claim 6 wherein, during a measuring step, the outer surfaces of the first cylinder and the second cylinder are coupled with each other via a layer of a material to be tested for tack, and the driver is activated, in which measuring step, the measuring signal delivered by the force sensor is processed by the processor as a measuring value, taking into account the first value stored in the processor in the first calibration step.

11. A device according to claim 8 wherein, during a measuring step, the outer surfaces of the first cylinder and the second cylinder are coupled with each other via a layer of a material to be tested for tack, and the driver is activated, in which measuring step, the measuring signal delivered by the force sensor is processed by the processor as a measuring value, taking into account the first and/or second correction value stored in the processor in the first calibration step and second calibration step.

12. A device according to claim 9 wherein, during a measuring step, the outer surfaces of the first cylinder and the second cylinder are coupled with each other via a layer of a material to be tested for tack, and the driver is activated, in which measuring step, the measuring signal delivered by the force sensor is processed by the processor as a measuring value, taking into account the first and/or second correction value stored in the processor in the first calibration step and second calibration step.

* * * * *